United States Patent
Jewson (10) Patent No.: US 11,270,382 B2
(45) Date of Patent: Mar. 8, 2022

(54) HIGH PERFORMANCE COMPUTING SYSTEM AND PLATFORM

(71) Applicant: Risk Management Solutions, Inc., Newark, CA (US)

(72) Inventor: Stephen Jewson, London (GB)

(73) Assignee: RISK MANAGEMENT SOLUTIONS, INC., Newark, CA (US)

(*) Notice: Subject to any disclaimer, the term of this patent is extended or adjusted under 35 U.S.C. 154(b) by 555 days.

(21) Appl. No.: 15/355,659

(22) Filed: Nov. 18, 2016

(65) Prior Publication Data

US 2017/0148105 A1    May 25, 2017

Related U.S. Application Data

(60) Provisional application No. 62/259,294, filed on Nov. 24, 2015.

(51) Int. Cl.
| | |
|---|---|
| *G06Q 40/08* | (2012.01) |
| *G06Q 10/06* | (2012.01) |
| *G16H 50/30* | (2018.01) |
| *G06F 30/20* | (2020.01) |
| *G16Z 99/00* | (2019.01) |

(52) U.S. Cl.
CPC ............ *G06Q 40/08* (2013.01); *G06F 30/20* (2020.01); *G06Q 10/06398* (2013.01); *G16H 50/30* (2018.01); *G16Z 99/00* (2019.02); *Y02A 90/10* (2018.01)

(58) Field of Classification Search
CPC .......... G06N 7/06; G06N 7/026; G06N 5/047; G06Q 40/08; G06Q 10/06398; G16Z 99/00; G16H 50/30; G06F 30/20; Y02A 90/10

USPC .............................................................. 705/4
See application file for complete search history.

(56) References Cited

U.S. PATENT DOCUMENTS

| | | | |
|---|---|---|---|
| 4,126,895 A * | 11/1978 | Weemaes | G06F 9/4825 713/502 |
| 2006/0184527 A1* | 8/2006 | Chi | H04L 43/028 |
| 2011/0202385 A1 | 8/2011 | Matsui et al. | |
| 2012/0221486 A1* | 8/2012 | Leidner | G06Q 10/0635 705/36 R |

(Continued)

FOREIGN PATENT DOCUMENTS

| | | |
|---|---|---|
| WO | WO 2014/205496 A1 | 12/2014 |
| WO | WO/2014/205496 A1 | 12/2014 |
| WO | WO 2015/153290 A1 | 10/2015 |

OTHER PUBLICATIONS

Dialog NPL (non-patent literature) Search Result, dated Nov. 5, 2021. (Year: 2021).*

(Continued)

*Primary Examiner* — Hai Tran
(74) *Attorney, Agent, or Firm* — Hickman Becker Bingham Ledesma LLP (57) ABSTRACT

A computing system and platform includes an event subsample processor and a risk item subsample processor to generate approximations when undertaking processing to model complex events in order to minimize CPU, memory and storage overhead. The event subsample processor approximates values associated with events based on a measure of the importance of select events; the risk item subsample processor groups similar event/risk item pairs and approximates values using representatives from each group.

15 Claims, 4 Drawing Sheets

(56) References Cited

U.S. PATENT DOCUMENTS

| | | |
|---|---|---|
| 2013/0332474 A1 | 12/2013 | Glaubman et al. |
| 2014/0142912 A1 | 5/2014 | Cipriani et al. |
| 2014/0278306 A1 | 9/2014 | Taghavi et al. |
| 2015/0019269 A1* | 1/2015 | Bonissone ............ G06Q 10/10 705/4 |
| 2016/0299944 A1 | 10/2016 | Isaacson et al. |

OTHER PUBLICATIONS

European Extended Search Report, European Application No. 16200326.3, dated Jan. 3, 2017, 7 pages.
U.S. Appl. No. 62/146,836, filed Apr. 13, 2015, Inventors Cory Isaacson et al.
European Patent Office, "Search Report" in application No. 16 200 326.3-1222, dated Jul. 28, 2020, 6 pages.
European Claims in application No. 16 200 326.3-1222, dated Jul. 2020, 4 pages.

* cited by examiner

HIGH PERFORMANCE COMPUTING SYSTEM AND PLATFORM

CROSS-REFERENCE TO RELATED APPLICATIONS

This application claims priority under 35 U.S.C. § 119(e) to U.S. Provisional Patent Application Ser. No. 62/259,294, "High Performance Computing System and Platform," filed on Nov. 24, 2015, which is incorporated herein by reference in its entirety.

FIELD

The subject matter described herein relates generally to data processing systems for modeling complex scenarios that involve massive amounts of data, and more specifically to systems optimized for sampling to reduce CPU, memory and storage requirements.

BACKGROUND

A data explosion has taken place over the past few decades. In almost every industry and field of endeavor, data and metadata have been generated, organized and stored to a degree never before seen. Satellite images are now publicly available from multiple sources for the entire globe. Weather and climatological data are likewise available on a worldwide basis. Other information, such as population density and demographics, electrical grid capacities, water resources, geopolitical records and the like is available via both free and paid services, whether from the public sector or the private sector.

While the availability of such data permits creation of services and systems never before possible, it also poses a tremendous technical challenge. With so much available data, analysis is now often limited by the ability of computing systems to quickly access to and process such data from any desired location.

To provide just one example, consider computerized modeling of catastrophe risks. To obtain meaningful predictions of damage or failure (e.g., train derailment, bridge collapse, building damage, road flooding), sufficient data are now available to, in theory, model a very large number (say, 100,000) versions of some future period via a computer simulation, wherein each simulated version consists of a simulated number of simulated catastrophe events, each of which includes a simulation of hazard values due to the catastrophe (e.g., wind speeds, flood depths) on a spatial grid. In this scenario, not every event affects each risk item (e.g., building). For each pairing of an event with a risk item a simulated hazard value at the location of the risk item can be considered, along with a corresponding damage function and damage distribution, to calculate a possible level of damage for the risk item. Then, simulated levels of damage for all event/risk item pairs, for all events, can be combined to create metrics that estimate distributions of possible total damages to the risk items under consideration. These damages can then be summarized using an appropriate metric, e.g., an average annual damage metric (sometimes referred to as AAD, and defined herein as the average of the annual damage for the complete list of risk items over the simulated versions of the future year).

To provide a more detailed example of such modeling, one might seek to quantify wind damage risk due to typhoons hitting Japan next year for a list of ten million buildings. For some purposes, it may be helpful to use a very large number of simulations, e.g., 100,000 possible versions of possible weather next year, which might contain 800,000 individual typhoons in total. If each typhoon affects, on average, only 10% of the buildings, that would still result in one million affected buildings to be modeled for each typhoon on average.

Such ambitious modeling efforts pose significant computer hardware challenges, imposing significant requirements for CPU capabilities, working memory as well as storage. Using the example above, for example, calculations would be required for 800 billion event/risk item pairs. If each calculated damage value is stored with 8 bytes, that corresponds to 6.4 Terabytes of data; holding such data in RAM, given current hardware availability, would require extremely expensive conventional computing components. Even that amount of disk storage, just for that one modeling exercise, would be significant.

Numerous attempts have been made to address such computational challenges. The most basic, brute force approach is to simply employ traditional parallel processing systems with massive memory and storage arrays to permit such modeling. In another approach, management of diverse sources of data using specialized computing structures to more efficiently process data in such circumstances is detailed in copending, commonly owned U.S. patent application 62/146,836, filed Apr. 13, 2015 (now corresponding to U.S. patent application Ser. No. 15/097,233, filed Apr. 12, 2016), the contents of which is hereby incorporated by reference as if fully set forth herein. Further discussion of related issues is provided in copending, commonly owned U.S. patent application Ser. No. 13/799,120 filed Mar. 13, 2013, published as US 2014/0278306, the contents of which is hereby incorporated by reference as if fully set forth herein.

Modeling of the sort discussed above can be applied to various fields and industry sectors, including agriculture (risks to farmland and agricultural products); supply chain (possible interruptions impacting certain vendors or procurement items); insurance (relating for instance to real property, people, or contents of buildings/containers); protection of governmental/municipal facilities (airports against weather or terrorism, dams and other flood defenses against storm water), energy (oil platforms, tankers and pipelines subject to leaks/spills); healthcare (ranging from disease prediction to analysis of possible pandemic/epidemic threats to personalized medicine procedure outcome prediction); and heavy industry (factory disruption based on events ranging from work stoppages to worker health to catastrophic events).

For each of these scenarios, an additional complexity may arise in that data structures for an item may be expressed as a nested hierarchy of a large number of attributes that may make use of a traditional relational database structure difficult or nearly impossible to use. Further discussion of such complexity is provided, for example, in copending commonly owned U.S. patent application Ser. No. 13/914,774, filed Jun. 11, 2013 and published as US 2013/0332474 and PCT application PCT/US2015-022776, filed Mar. 26, 2015, the contents of which are hereby incorporated by reference as if fully set forth herein.

The resulting data analysis challenges make it difficult to use conventional computing systems. For instance, conventional model computation constructs a given model as a single large function and is known as "monolithic model implementation." Typically, this is implemented using a primary programmatic loop over repeating elements, represented in pseudo-code as:

for each Event
   for each Item
      model extent of damage or failure This approach is referred to as event/item loop processing. For each iteration of the loop, the extent of damage or failure needs to be computed, which can quickly result in data and computational "explosions" as the number of events and items increases. Some attempts have been made to use columnar databases in such applications, but these have their own scaling issues and columnar databases are typically not well-suited for supporting complex object types.

Rather than using computing systems with typical, known architectures, it would be desirable if a computing system with an architecture that inherently allows use of smaller, less expensive computer hardware were available for such complex calculations.

The features and advantages described in the specification are not all inclusive and, in particular, many additional features and advantages will be apparent to one of ordinary skill in the art in view of the drawings and text herein. Moreover, it should be noted that the language used in the text has been principally selected for readability and instructional purposes, and may not have been selected to delineate or circumscribe the disclosed subject matter.

DETAILED DESCRIPTION OF THE DRAWINGS

General System Architecture

Figure 1:
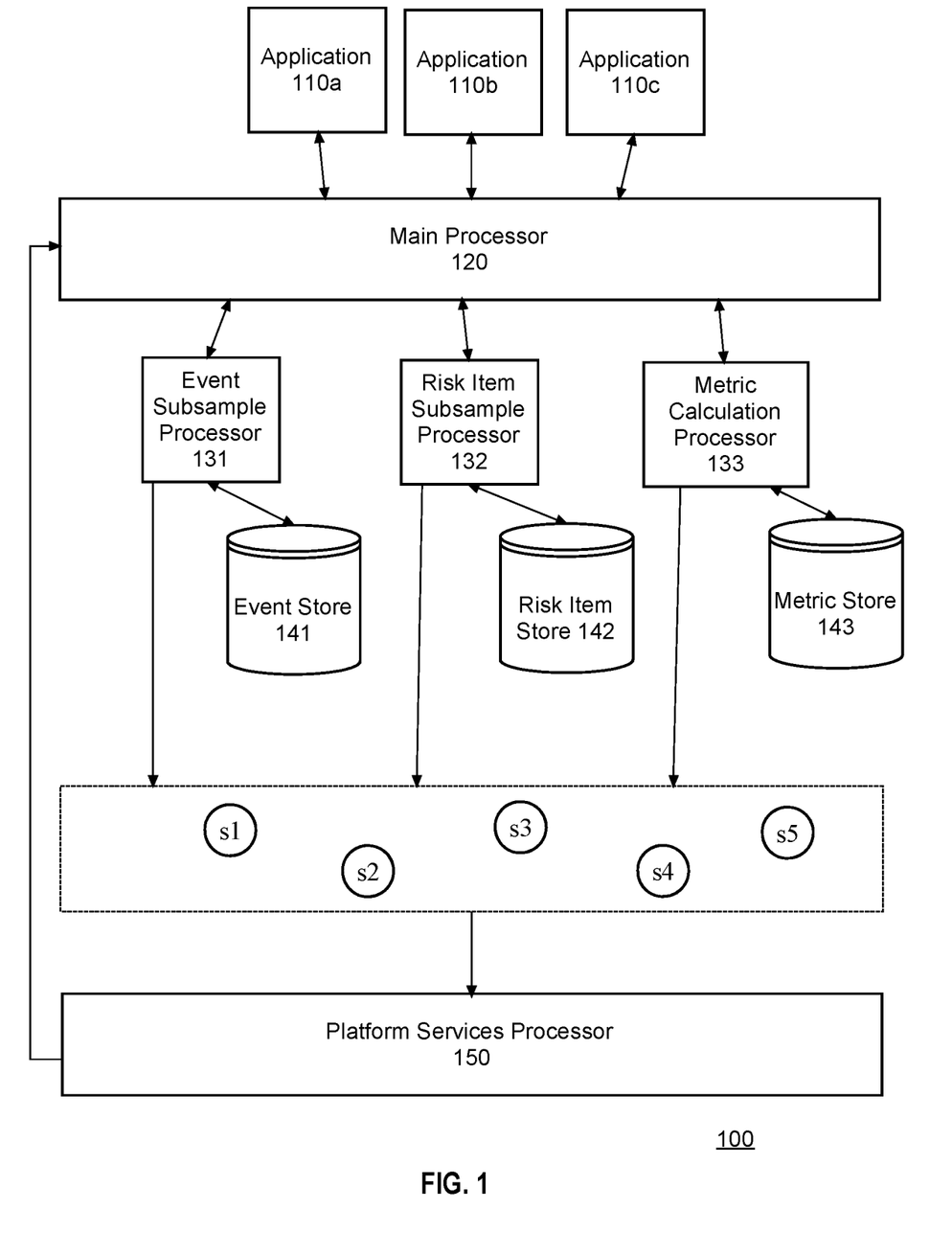
FIG. 1 is an illustration of a computing system according to one embodiment.

As described herein, a computing system 100 includes a main processor 120 facilitating communicating between a variety of applications 110 providing modeling requests and processors 131-133, including an event subsample processor 131, a risk item subsample processor 132, and a metric calculation processor 133, each of which has access to a corresponding data store 141, 142, 143. The data stores are of varying types, depending on the scale and nature of the data that they handle. In some embodiments, the operation of these processors results in data streams (s1 . . . s9) that are sent to a platform services processor 150 for operation in accordance with the applications 110.

The systems described herein can be used for a variety of purposes ranging from municipal planning to loss prediction to supply chain management. Categories of use include, but are not limited to, personnel assignments, resource and asset (e.g. spare equipment) allocation, maintenance scheduling and completion, location planning and business case support (particularly for larger commercial and industrial facilities where critical infrastructure failures can interrupt operations), corporate disaster planning and response, and analysis of other similar scenarios involving allocation of limited or time-sensitive resources.

Subsample and Approximation Processors

In order to reduce CPU, memory and storage requirements, event subsample processor 131 and risk item subsample processor 132 are arranged to select event/risk item pairs for processing and storage, and metric calculation processor 133 is arranged to generate, in the example of catastrophe risk modeling set forth above, metrics such as an average annual damage metric for the desired simulation. In other catastrophe risk modeling situations, other metrics than AAD may be used, and in still other applications, other metrics are used as may be most appropriate to the task at hand. In some embodiments, only event subsampling is used; in others only risk item subsampling is used. Should a particular application present opportunities for CPU, memory or storage reduction from both types of subsampling, an embodiment using both is employed. In various embodiments event subsample processor 131 and risk item subsample processor 132 are implemented using a common processor (either the same as main processor 120 or otherwise). Main processor 120 is in some embodiments a processor used for tasks not specific to subsampling as described herein, e.g., interfacing with applications 110.

Figure 2:
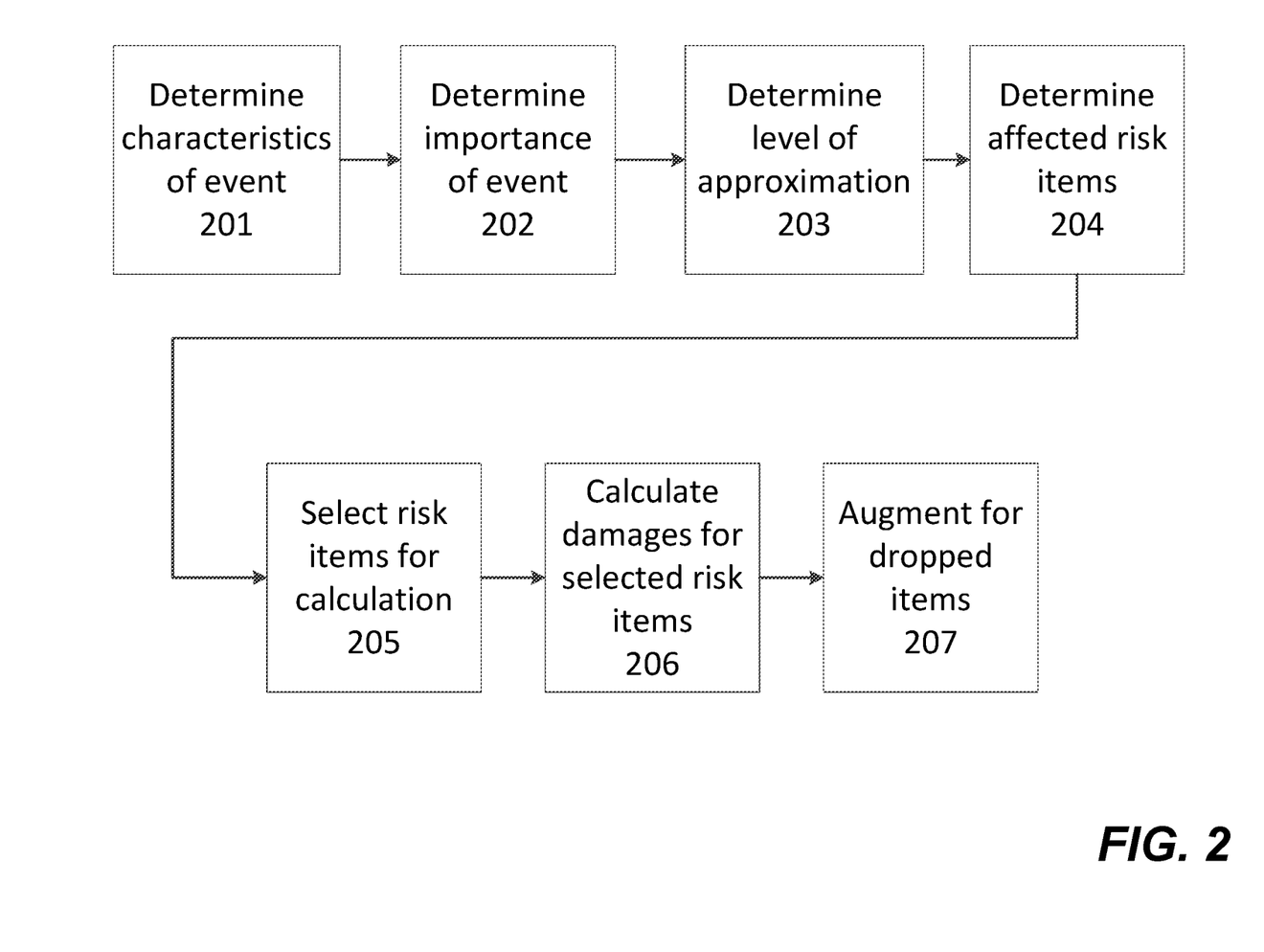
FIG. 2 illustrates operation of an event subsample processor according to one embodiment.

Event subsample processor 131 is configured to undertake an approximation process based on a determined importance of each simulated event, in relation to the metric of interest. Referring now also to FIG. 2, in one embodiment, event subsample processor uses approximation processing to estimate the impact of each simulated event by implementing the following method that recognizes each simulated event is not equally important to determination of AAD. Initially, certain characteristics of the event are determined 201. Using the example of a typhoon, the location, maximum sustained wind speed and duration of the event may be such characteristics. Next, an importance of the event is determined 202. In some applications, the importance is tied directly to the characteristics of the event previously determined. For example, in some embodiments a typhoon located over a country's capital city is considered a more important event than one over a rural area; a Category 5 typhoon is considered more important than a Category 3 storm, and a slower moving, more sustained typhoon is considered more important than one that quickly passes over a location of interest. However, a modeling problem may suggest other measures of importance as well, such as prior estimates of the possible damage, or spatial variability of that damage.

Based on determination of the importance of the event, a level of approximation for the event is then determined 203. This level of approximation determines what level of sampling will be applied for the event, as detailed below. In one embodiment, a percentage of risk items is selected for sampling, based on the importance of the event.

As detailed generally above, each simulated event has a corresponding set of affected risk items, and those are determined 204. In some embodiments, this is done after determining the characteristics, importance, and level of approximation (201-203), while in other embodiments it is done before, in parallel, or otherwise.

Next, the affected risk items are selected 205 for calculation, consistent with the level of approximation chosen for the event. In one embodiment, this is done by randomly selecting each risk item to be used in calculating damages or ignored, based on the desired level of approximation. For instance, if a desired level of approximation for a particular event is 75%, a random number generator may be used to generate numbers between 1 and 100 for each risk item impacted by that event, and risk items for which the random number is between 1 and 75 are selected for use in calculations while those with the random number between 76 and 100 are dropped from further consideration. Those skilled in the art will recognize that numerous other methods may be used to select risk items consistent with a desired level of approximation. Furthermore, in actual application, it may be that a far smaller subsampling rate is used than the 75% mentioned here for illustrative purposes. For truly massive modeling problems, subsampling on the order of $10^{-5}$ or lower for some of the events in the set of all events may yield usable approximations while dramatically reducing computational overhead. The damages for each selected items are then calculated 206. Since a number of risk items were ignored, the damages thus calculated are augmented (i.e., increased) 207 by a corresponding amount, or an approximate estimate of the corresponding amount. For instance, if only 75% of the risk items are calculated in 206, those damages are multiplied by (1/0.75) or (4/3) to obtain the approximation of the expected damages value for that event.

Alternative embodiments are similar with some modifications from what is described above. For instance, in some embodiments hazard characteristics for an event are used before any damages have been calculated, as the basis for the probability (i.e., level of approximation) that is to be used in the sampling. In other, probability is based on damages calculated for each risk item affected by the event, which may not save calculation overhead but instead merely reduces required disk storage. Note that in some instances, this may also be appropriate where modeling inputs already include such damages, so there is no additional processing overhead to reduce. In yet others, probability of retaining risk items is based on a proxy for characteristics of damages calculated for each event, such as a simplified damage determination or a damage calculation for different but similar sets of risk items.

Figure 3:
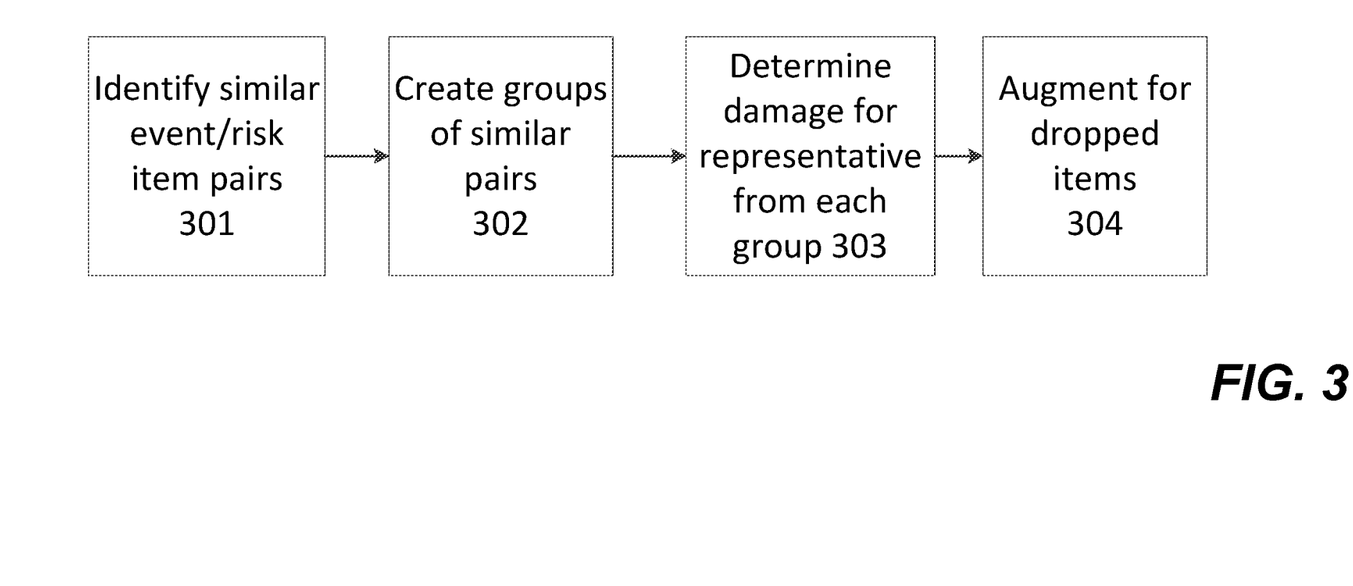
FIG. 3 illustrates operation of a risk item subsample processor according to one embodiment.

In other applications, it may be more efficient to use risk item subsample processor 132 as the basis for determining AAD or other metrics. Referring now also to FIG. 3, in one embodiment risk item subsample processor operates by implementing the following method. First, event/risk pairs that might be expected to have similar damage values are identified 301. In some embodiments, this is done without doing any damages calculations, but based instead on heuristics or extremely simplified characteristics (e.g., identifying all buildings that are residences, all that are offices, all that are retail stores, and all that are factories; or identifying building/event pairs in which buildings are affected by the same or similar hazard values). Next, the similar pairs are grouped together 302. For each group, a representative one (or in some embodiments small subset) of items are then processed to determine a damage value 303. The overall damage value for the group is then augmented by accounting for dropped items using techniques corresponding to those discussed for augmenting 207 of FIG. 2. Overall approximated AAD is then determined as discussed in connection with FIG. 2.

As mentioned above, in some modeling instances truly massive numbers of individual event/risk item pairs may exist in a model (800 billion for the example provided earlier). The precise value of many of those pairs, however, may be relatively insignificant in determining the overall approximated AAD. For instance, a typhoon event may impact both residences and commercial/industrial facilities, and variations in residential property values (or damage amounts) may be extremely small compared to variations in, say, corresponding values for factories. Therefore, in some embodiments subsampling is accomplished recognizing this difference, for instance by sampling pairs corresponding to residences with far lower frequency than pairs corresponding to factories.

In some embodiments, the critical concern may not be processing overhead but storage requirements, so similar techniques are applied in those embodiments after damage calculations (which also allows much more accurate grouping of pairs with similar values).

The description above has been phrased for purposes of clarity in illustration. Those skilled in the art will recognize that certain structures and techniques differing from those described here may be preferred in certain circumstances. For example, in many applications it may be preferable for risk item subsample processor 132 to not actually generate groups at all, but to effectively do so via application of a statistical algorithm. In such an algorithm the importance of each event/risk pair is determined, and used to determine a sampling proportion for that event/risk pair. That sampling proportion is then used to randomly select the event/risk pairs to be used in calculating damages, or ignored. Since a number of event/risk pairs are ignored, damages are then augmented by a corresponding amount, or an approximate estimate of the corresponding amount. Likewise, variations in the configuration of risk item subsample processor 132 similar to those discussed in connection with event subsample processor 131 are used in various embodiments as the application may require.

Event subsample processor 131 and risk item subsample processor 132 can also be used in some embodiments together, each to solve portions of a modeling effort most amenable to efficiencies it provides, or together in an integrated manner. In the latter case event subsample processor 131 is used to subsample events based on a measure of importance for each event, and risk item subsample processor 132 is used to further subsample risks within that event based on a measure of importance of each individual event/risk pair.

Computing Device

Figure 4:
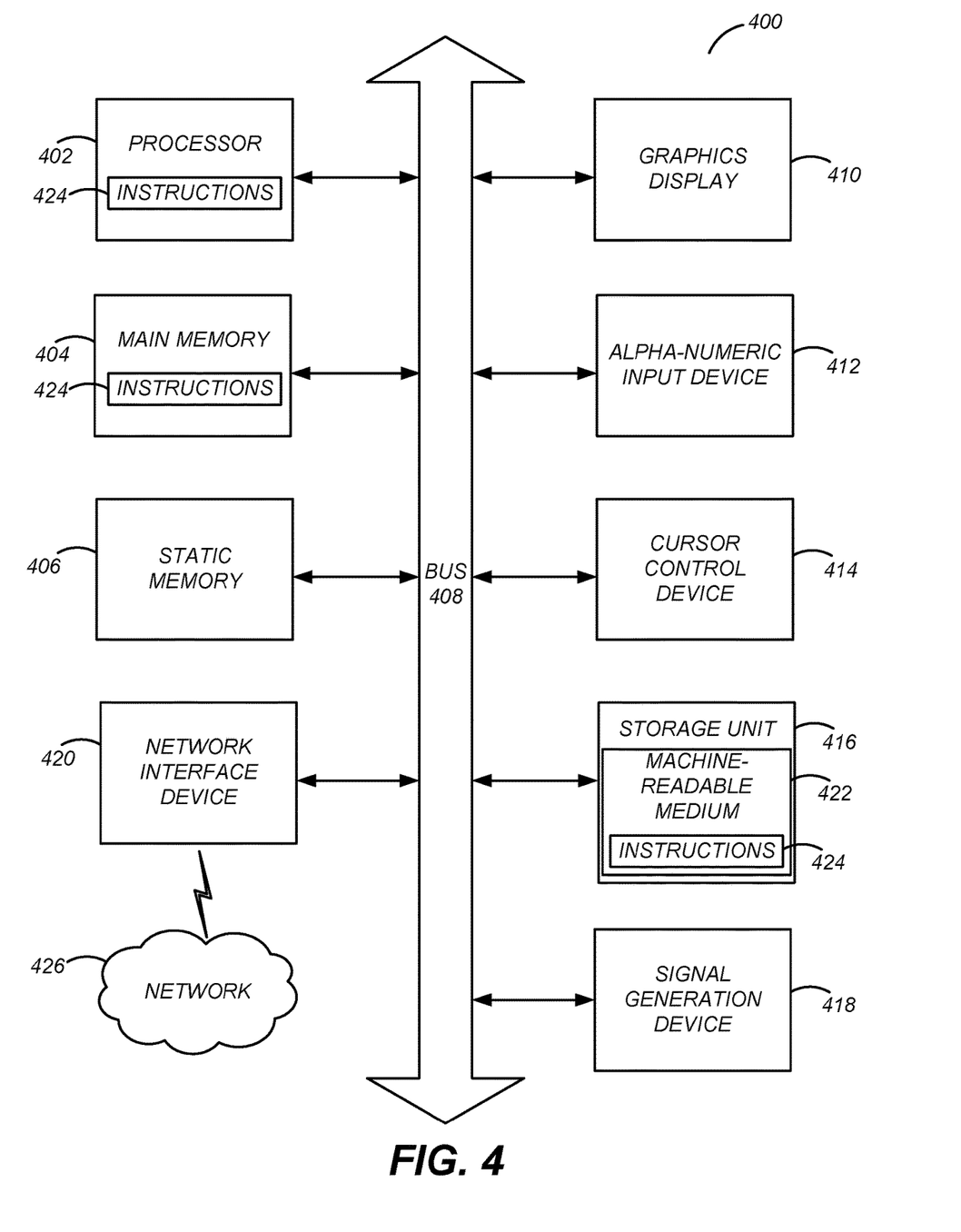
FIG. 4 is a block diagram illustrating components of an example machine able to read instructions from a machine-readable medium and execute them in a processor (or controller) according to one embodiment.

FIG. 4 is a block diagram illustrating components of an example machine able to read instructions from a machine-readable medium and execute them in a processor (or controller). Specifically, FIG. 4 shows a diagrammatic representation of a machine in the example form of a computer system 400 within which instructions 424 (e.g., software) for causing the machine to perform any one or more of the methodologies discussed herein may be executed. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 424 (sequential or otherwise) that specify actions to be taken by that machine. Further, while only a single machine is illustrated, the term "machine" shall also be taken to include any collection of machines that individually or jointly execute instructions 424 to perform any one or more of the methodologies discussed herein.

The example computer system 400 includes a processor 402 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 404, and a static memory 406, which are configured to communicate with each other via a bus 408. The computer system 400 may further include graphics display unit 410 (e.g., a plasma display panel (PDP), a liquid crystal display (LCD), a projector, or a cathode ray tube (CRT)). The computer system 400 may also include alphanumeric input device 412 (e.g., a keyboard), a cursor control device 414 (e.g., a mouse, a trackball, a joystick, a motion sensor, or other pointing instrument), a storage unit 416, a signal generation device 418 (e.g., a speaker), and a network interface device 420, which also are configured to communicate via the bus 408.

The storage unit 416 includes a machine-readable medium 422 on which is stored instructions 424 (e.g., software) embodying any one or more of the methodologies or functions described herein. The instructions 424 (e.g., software) may also reside, completely or at least partially, within the main memory 404 or within the processor 402 (e.g., within a processor's cache memory) during execution thereof by the computer system 400, the main memory 404 and the processor 402 also constituting machine-readable media. The instructions 424 (e.g., software) may be transmitted or received over a network 426 via the network interface device 1420.

While machine-readable medium 422 is shown in an example embodiment to be a single medium, the term "machine-readable medium" should be taken to include a single medium or multiple media (e.g., a centralized or distributed database, or associated caches and servers) able to store instructions (e.g., instructions 424). The term "machine-readable medium" shall also be taken to include any medium that is capable of storing instructions (e.g., instructions 424) for execution by the machine and that cause the machine to perform any one or more of the methodologies disclosed herein. The term "machine-readable medium" includes, but not be limited to, data repositories in the form of solid-state memories, optical media, and magnetic media.

System 100, as well as the other processing devices detailed herein, in various embodiments, are implemented using one or more computers configured such as computer 400 discussed above. Those of skill in the art will recognize that based on processing requirements, several various components may be implemented on a common one of such computers, or several of such computers can operate in a collaborative fashion to implement one or more of such components.

Other Considerations

While particular embodiments are described, it is to be understood that modifications will be apparent to those skilled in the art without departing from the spirit of the disclosures herein. The scope of any disclosure is not limited to the specific embodiments described herein. Other embodiments, uses and advantages of the disclosures will be apparent to those skilled in art from consideration of the specification and practice of the embodiments disclosed herein.

The embodiments herein have been described in particular detail with respect to several possible embodiments. Those of skill in the art will appreciate that the subject matter may be practiced in other embodiments. The particular naming of the components, capitalization of terms, the attributes, data structures, or any other programming or structural aspect is not mandatory or significant, and the mechanisms that implement various embodiments may have different names, formats, or protocols. Further, the systems may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some portions of above description present the features of the embodiments in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "determining" or the like, refer to the action and processes of a computer system, or similar electronic computing device, that manipulates and transforms data represented as physical (electronic) quantities within the computer system memories or registers or other such information storage, transmission or display devices.

The described embodiments also relate to an apparatus for performing the operations herein. This apparatus may be specially constructed for the various purposes, or it may comprise a computer selectively activated or reconfigured by a computer program stored on a computer readable medium that can be accessed by the computer and run by a computer processor. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, unless context dictates otherwise, the computers referred to in the specification may include a single processor or may be architectures employing multiple processor designs for increased computing capability.

In addition, the described embodiments are not described with reference to any particular programming language. It is appreciated that a variety of programming languages may be used to implement the teachings as described herein.

The described embodiments are well suited to a wide variety of computer network systems over numerous topologies. Within this field, the configuration and management of large networks comprise storage devices and computers that are communicatively coupled to dissimilar computers and storage devices over a network, such as the Internet.

Finally, it should be noted that the language used in the specification has been principally selected for readability and instructional purposes, and may not have been selected to delineate or circumscribe the subject matter. Accordingly, the disclosure is intended to be illustrative, but not limiting.

Upon reading this disclosure, those of skill in the art will appreciate still additional alternative structural and functional designs for a system and a process for providing high performance big data computing through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope of the disclosure.

What is claimed is:

1. A computer system for modeling damages associated with a plurality of events, comprising:
    an event data store storing data corresponding to a plurality of events and characteristics of each of the plurality of events;
    a risk item data store storing data corresponding to a plurality of risk items;
    a main processor configured to perform, with respect to a resource utilization limitation on processing overhead on storage overhead for the computer system:
    identifying an item to which the resource utilization limitation is applied;
    when the item is storage overhead but not processing overhead, causing an event subsample processor or a risk item subsample processor to perform specific steps based on damage values or characteristics:
    the event subsample processor being configured to perform:
        for each event of the plurality of events in an event data store, determining an event importance indicator of the event;
        for each event of the plurality of events, calculating damage values or damage characteristics for each risk item of the plurality of risk items affected by the event;
        for each of the plurality of events, sampling risk items from the risk items affected by the event based on the corresponding event importance indicator and corresponding damage values or damage characteristics, the plurality of events and sampled risk items forming event-based sampled event/risk pairs; and
        estimating damages based on the damage values or damage characteristics for the event-based sampled event/risk pairs;
    the risk item subsample processor being configured to perform:
        for each event/risk pair of a group of event/risk pairs formed from the plurality of events and a set of risk items of the plurality of risk items affected by the plurality of events, determining a pair importance indicator of the event/risk pair;
        for each event of the plurality of events, calculating damage values or damage characteristics for each risk item of the plurality of risk items affected by the event;
        sampling event/risk pairs from the group of event/risk pairs based on the pair importance indicators and the corresponding damage values or damage characteristics to obtain risk-based sampled event/risk pairs; and
        estimating damages based on the damage values or damage characteristics for the risk-based sampled event/risk pairs;
    when the item is processing overhead, causing the event subsample processor or the risk item subsample processor to perform:
    the event subsample processor being configured to perform:
        for each event of the plurality of events in an event data store, determining an event importance indicator of the event;
        for each of the plurality of events, sampling risk items from the plurality of risk items affected by the event based on the corresponding event importance indicator, the plurality of events and sampled risk items forming event-based sampled event/risk pairs; and
        estimating damages for the event-based sampled event/risk pairs; and
    the risk item subsample processor being configured to perform:
        for each event/risk pair of a group of event/risk pairs formed from the plurality of events and the pluralities of risk items affected by the plurality of events, determining a pair importance indicator of the event/risk pair;
        sampling event/risk pairs from the group of event/risk pairs based on the pair importance indicators to obtain risk-based sampled event/risk pairs; and
        estimating damages for the risk-based sampled even/risk pairs.

2. The computer system of claim 1, further comprising:
    a metric data store storing data corresponding to a plurality of metrics,
    the main processor being in operative communication with a plurality of applications; and
    a metric calculation processor in operative communication with the main processor and configured to access the metric data store,
    wherein, the event subsample processor, the event data store, the risk item subsample processor, the risk item data store, the metric calculation processor and the metric data store are configured to produce a data stream,
    wherein the computer system further comprises a platform services processor being configured to recieve the data stream and operating thereon in accordance with a particular application.

3. The computer system of claim 1, each of the plurality of events being associated with catastrophic risks.

4. The computer system of claim 1, wherein the resource utilization limitation is based on a memory requirement.

5. The computer system of claim 1, wherein the resource utilization limitation is based on a disk storage requirement.

6. The computer system of claim 1, wherein determining the event importance indicator is performed based on a nature of the event, a location where the event is expected to occur, prior estimates of possible damages from the event, or spatial variability of the event.

7. The computer system of claim 1, the plurality of risk items including buildings or other physical entities to which the plurality of events occur.

8. A method of modeling damages associated with a plurality of events with respect to a resource utilization limitation on processing overhead on storage overhead for a computer system, comprising:

maintaining an event data store storing data corresponding to a plurality of events and characteristics of each of the plurality of events;
maintaining a risk item data store storing data corresponding to a plurality of risk items;
identifying an item to which the resource utilization limitation is applied;
when the item is storage overhead but not processing overhead, causing an event subsample processor or a risk item subsample processor to perform specific steps based on damage values or characteristics:
the event subsample processor being configured to perform:
for each event of the plurality of events in an event data store, determining an event importance indicator of the event;
for each event of the plurality of events, calculating damage values or damage characteristics for each risk item of the plurality of risk items affected by the event;
for each of the plurality of events, sampling risk items from the risk items affected by the event based on the corresponding event importance indicator and corresponding damage values or damage characteristics, the plurality of events and sampled risk items forming event-based sampled event/risk pairs; and
estimating damages based on the damage values or damage characteristics for the event-based sampled event/risk pairs;
the risk item subsample processor being configured to perform:
for each event/risk pair of a group of event/risk pairs formed from the plurality of events and a set of risk items of the plurality of risk items affected by the plurality of events, determining a pair importance indicator of the event/risk pair;
for each event of the plurality of events, calculating damage values or damage characteristics for each risk item of the plurality of risk items affected by the event;
sampling event/risk pairs from the group of event/risk pairs based on the pair importance indicators and the corresponding damage values or damage characteristics to obtain risk-based sampled event/risk pairs; and
estimating damages based on the damage values or damage characteristics for the risk-based sampled event/risk pairs;
when the item is processing overhead, causing the event subsample processor or the risk item subsample processor to perform:
the event subsample processor being configured to perform:
for each event of the plurality of events in an event data store, determining an event importance indicator of the event;
for each of the plurality of events, sampling risk items from the plurality of risk items affected by the event based on the corresponding event importance indicator, the plurality of events and sampled risk items forming event-based sampled event/risk pairs; and
estimating damages for the event-based sampled event/risk pairs; and
the risk item subsample processor being configured to perform:
for each event/risk pair of a group of event/risk pairs formed from the plurality of events and the pluralities of risk items affected by the plurality of events, determining a pair importance indicator of the event/risk pair;
sampling event/risk pairs from the group of event/risk pairs based on the pair importance indicators to obtain risk-based sampled event/risk pairs; and
estimating damages for the risk-based sampled even/risk pairs.

9. The method of claim 8, wherein determining the event importance indicator is performed based on a nature of the event, a location where the event is expected to occur, prior estimates of possible damages from the event, or spatial variability of the event.

10. The method of claim 8, wherein the plurality of risk items including buildings or other physical entities to which the plurality of events occur.

11. The method of claim 8, further comprising for each risk item of the plurality of risk items, generating a_data stream_corresponding to the risk item paired with the event, for processing in accordance with a particular application.

12. A non-transitory computer-readable storage medium comprising executable computer program code for modeling damages associated with a plurality of events with respect to a resource utilization limitation on processing overhead on storage overhead for a computer system, the computer program code comprising instructions which, when executed by a main processor, cause:
maintaining an event data store storing data corresponding to a plurality of events and characteristics of each of the plurality of events;
maintaining a risk item data store storing data corresponding to a plurality of risk items;
identifying an item to which the resource utilization limitation is applied;
when the item is storage overhead but not processing overhead, causing an event subsample processor or a risk item subsample processor to perform specific steps based on damage values or characteristics:
the event subsample processor being configured to perform:
for each event of the plurality of events in an event data store, determining an event importance indicator of the event;
for each event of the plurality of events, calculating damage values or damage characteristics for each risk item of the plurality of risk items affected by the event;
for each of the plurality of events, sampling risk items from the risk items affected by the event based on the corresponding event importance indicator and corresponding damage values or damage characteristics, the plurality of events and sampled risk items forming event-based sampled event/risk pairs; and
estimating damages based on the damage values or damage characteristics for the event-based sampled event/risk pairs;
the risk item subsample processor being configured to perform:
for each event/risk pair of a group of event/risk pairs formed from the plurality of events and a set of risk items of the plurality of risk items affected by the plurality of events, determining a pair importance indicator of the event/risk pair;
for each event of the plurality of events, calculating damage values or damage characteristics for each risk item of the plurality of risk items affected by the event;

sampling event/risk pairs from the group of event/risk pairs based on the pair importance indicators and the corresponding damage values or damage characteristics to obtain risk-based sampled event/risk pairs; and estimating damages based on the damage values or damage characteristics for the risk-based sampled event/risk pairs;

when the item is processing overhead, causing the event subsample processor or the risk item subsample processor to perform:

the event subsample processor being configured to perform:

for each event of the plurality of events in an event data store, determining an event importance indicator of the event;

for each of the plurality of events, sampling risk items from the plurality of risk items affected by the event based on the corresponding event importance indicator, the plurality of events and sampled risk items forming event-based sampled event/risk pairs; and     estimating damages for the event-based sampled event/risk pairs; and the risk item subsample processor being configured to perform:

for each event/risk pair of a group of event/risk pairs formed from the plurality of events and the pluralities of risk items affected by the plurality of events, determining a pair importance indicator of the event/risk pair;

sampling event/risk pairs from the group of event/risk pairs based on the pair importance indicators to obtain risk-based sampled event/risk pairs; and     estimating damages for the risk-based sampled even/risk pairs.

13. The non-transitory computer-readable storage medium of claim 12, wherein determining the event importance indicator is performed based on a nature of the event, a location where the event is expected to occur, prior estimates of possible damages from the event, or spatial variability of the event.

14. The non-transitory computer-readable storage medium of claim 12, the plurality of risk items including buildings or other physical entities to which the plurality of events occur.

15. The non-transitory computer-readable storage medium of claim 12, the computer program code further comprising instructions for, for each risk item of the plurality of risk items, generating a data stream corresponding to the risk item paired with the event for processing in accordance with a particular application.

* * * * *

UNITED STATES PATENT AND TRADEMARK OFFICE
CERTIFICATE OF CORRECTION

| | |
|---|---|
| PATENT NO. | : 11,270,382 B2 |
| APPLICATION NO. | : 15/355659 |
| DATED | : March 8, 2022 |
| INVENTOR(S) | : Stephen Jewson |

It is certified that error appears in the above-identified patent and that said Letters Patent is hereby corrected as shown below:

In the Claims

Claim 2, Column 10, Line 46, delete "recieve", insert --receive--

Signed and Sealed this
Seventeenth Day of May, 2022

Katherine Kelly Vidal
*Director of the United States Patent and Trademark Office*